United States Patent
Saitou et al.

(10) Patent No.: US 10,416,069 B2
(45) Date of Patent: Sep. 17, 2019

(54) PARTICLE COUNTER

(71) Applicant: RION Co., Ltd., Tokyo (JP)

(72) Inventors: Mitsuaki Saitou, Tokyo (JP); Masaki Shimmura, Tokyo (JP); Tomonobu Matsuda, Tokyo (JP); Yuki Yamakawa, Tokyo (JP)

(73) Assignee: RION Co., Ltd., Tokyo (JP)

( * ) Notice: Subject to any disclaimer, the term of this patent is extended or adjusted under 35 U.S.C. 154(b) by 0 days.

(21) Appl. No.: 16/200,511

(22) Filed: Nov. 26, 2018

(65) Prior Publication Data
US 2019/0162645 A1    May 30, 2019

(30) Foreign Application Priority Data

Nov. 28, 2017    (JP) .................. 2017-227734

(51) Int. Cl.
*G01N 15/14*    (2006.01)

(52) U.S. Cl.
CPC . *G01N 15/1429* (2013.01); *G01N 2015/1486* (2013.01); *G01N 2015/1493* (2013.01)

(58) Field of Classification Search
CPC ........... G01N 15/0205; G01N 15/1429; G01N 15/1434; G01N 2015/1454; G01N 2015/1486; G01N 2015/1488; G01N 2015/1493; G01N 21/45; G01B 9/02024; G01B 9/02038
See application file for complete search history.

(56) References Cited

U.S. PATENT DOCUMENTS 9,823,190 B2 *  11/2017  Minakami ............. G01N 21/53
9,983,113 B2     5/2018  Matsuda
(Continued)

FOREIGN PATENT DOCUMENTS

JP    H07103878 A    4/1995
JP    H08210347 A    8/1996
(Continued)

OTHER PUBLICATIONS

Varghese, Babu et al. "High angle phase modulated low coherence interferometry for path length resolved Doppler measurements of multiply scattered light". Optics Communications 281, 2008, pp. 494-498. (Year: 2008).*
(Continued)

*Primary Examiner* — Michael A Lyons
(74) *Attorney, Agent, or Firm* — Rankin, Hill & Clark LLP

(57) ABSTRACT

A particle counter provided with: a detector configured to receive interference light by scattered light and reference light with a light receiving element, and generate a detection signal corresponding to the interference light; a filter configured to perform, with respect to the detection signal generated by the detector, a filtering process for passing a frequency component corresponding to an intensity change of the interference light; a determination unit configured to determine, from a peak level of the detection signal before filtering and a peak level of the detection signal after filtering, whether the detection signal is due to a particle; and a counting unit configured to perform, if it is determined by the determination unit that the detection signal is due to the particle, particle counting based on the detection signal after filtering.

4 Claims, 8 Drawing Sheets

(56) References Cited

U.S. PATENT DOCUMENTS

| | | | |
|---|---|---|---|
| 10,054,529 B2 | 8/2018 | Matsuda | |
| 2002/0031737 A1* | 3/2002 | Von Drasek | G01N 21/39 431/79 |
| 2011/0001969 A1* | 1/2011 | Ishii | G01J 3/4412 356/337 |
| 2014/0152986 A1* | 6/2014 | Trainer | G01N 15/0205 356/336 |
| 2017/0160178 A1 | 6/2017 | Matsuda | |
| 2018/0038781 A1 | 2/2018 | Matsuda | |
| 2018/0259441 A1* | 9/2018 | Johnson | G01N 15/0227 |

FOREIGN PATENT DOCUMENTS

| | | |
|---|---|---|
| JP | 2003270120 A | 9/2003 |
| JP | 5859154 B1 | 2/2016 |
| JP | 2017102068 A | 6/2017 |

OTHER PUBLICATIONS

Japanese Office Action dated Jul. 19, 2018 for the corresponding Japanese Patent Application No. 2017-227734.
Decision to Grant dated Sep. 20, 2018 for the corresponding Japanese Patent Application No. 2017-227734.

* cited by examiner

PARTICLE COUNTER

CROSS-REFERENCE TO RELATED APPLICATION

This application claims priority from Japanese Patent Application Nos. 2017-227734 filed with the Japan Patent Office on Nov. 28, 2017, the entire content of which is hereby incorporated by reference.

BACKGROUND

1. Technical Field

The present disclosure relates to a particle counter.

2. Description of the Related Art

A particle counter is a device for measuring particles in a fluid that may include a liquid such as a chemical solution and water, or a gas such as air. In a particle counter, light from a light source is separated into irradiation light and reference light, and a fluid including particles is irradiated with the irradiation light. Scattered light from the particles due to the irradiation light is caused to interfere with the reference light, and the particles are counted for each particle size on the basis of interference light (see Japanese Patent No. 5859154).

SUMMARY

A particle counter including: a light source that emits light; a light superimposition unit configured to superimpose two lights in a space; an irradiation optical system configured to irradiate a fluid flowing in a flow passage with one light among a plurality of lights obtained by branching the light from the light source to form a detection area; a detection optical system configured to make a scattered light in a direction different from an optical axis of the irradiation optical system, among scattered lights from particles contained in the fluid in the detection area, enter the light superimposition unit; a reference optical system configured to make another one light among the plurality of lights enter the light superimposition unit as a reference light; a detector configured to receive an interference light by the scattered light and the reference light with a light receiving element, the interference light being obtained by the light superimposition unit, the detector being configured to generate a detection signal corresponding to the interference light; a filter configured to perform, with respect to the detection signal generated by the detector, a filtering process for passing a frequency component corresponding to an intensity change of the interference light; a determination unit configured to determine, from a peak level of the detection signal before filtering and a peak level of the detection signal after filtering, whether the detection signal is due to the particle, according to a predetermined calculation formula; and a counting unit configured to perform, if it is determined by the determination unit that the detection signal is due to the particle, particle counting based on the detection signal after filtering, and not to perform, if it is not determined by the determination unit that the detection signal is due to the particle, the particle counting based on the detection signal after filtering, wherein: the predetermined calculation formula is (Vp1−Vp2)/Vp1 for determining an attenuation rate from the peak level Vp1 of the detection signal before filtering to the peak level Vp2 of the detection signal after filtering.

DESCRIPTION OF THE EMBODIMENTS

Figure 1:
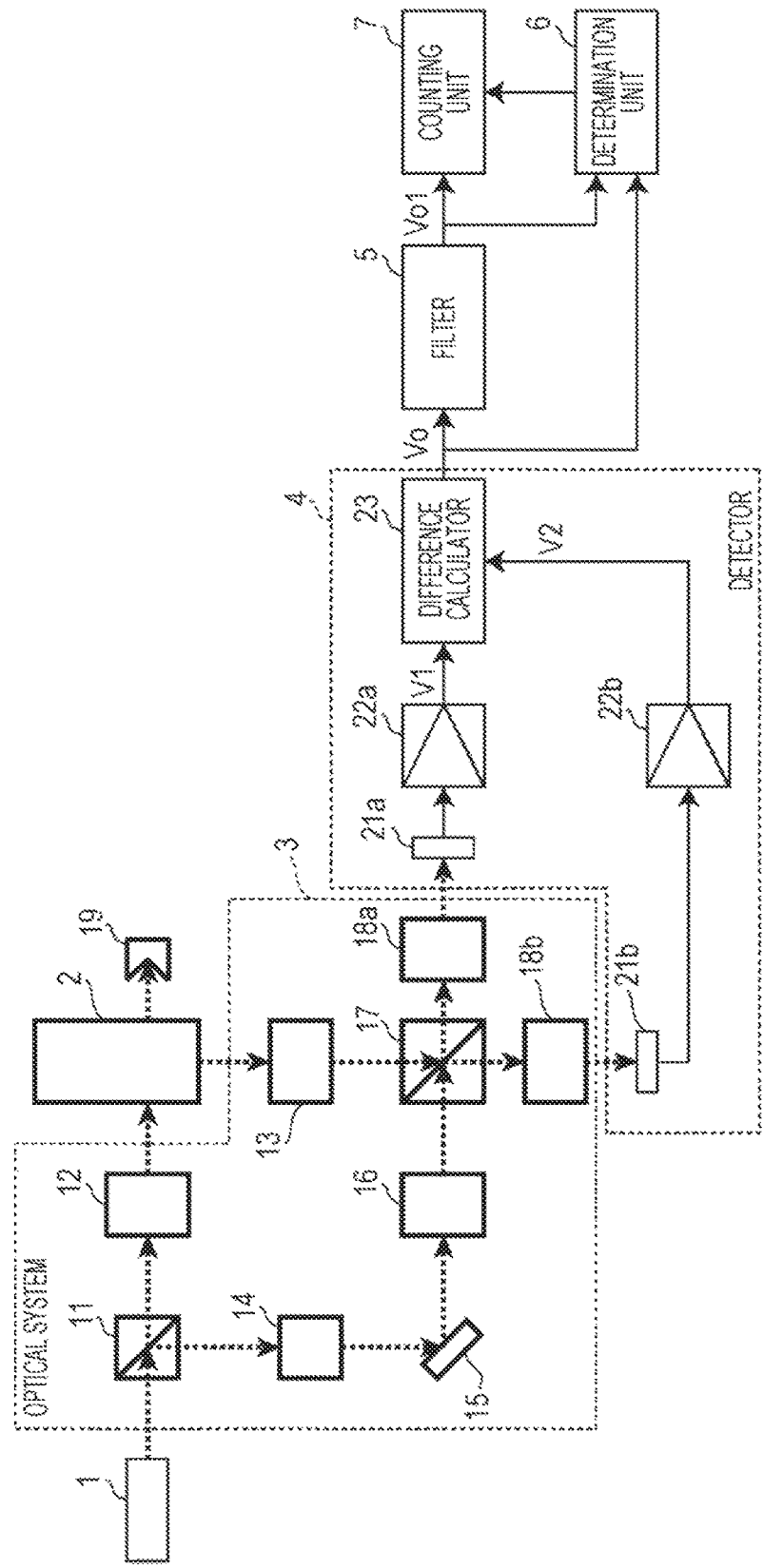
FIG. 1 is a block diagram of a configuration of a particle counter according to the first embodiment of the present disclosure.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In the particle counter discussed above, in order to increase the interference light intensity, the reference light intensity is increased because the scattered light intensity of the particles is low. When the reference light intensity is increased, a light receiving element receives an increased amount of light. As a result, shot noise during photoelectric conversion in the light receiving element increases. The noise hinders an accurate particle measurement.

In a detector that detects a detection signal corresponding to the interference light, spike noise may become superimposed on the detection signal due to electrical factors. In this case, the noise level can be lowered by filtering. However, depending on the intensity of the spike noise, false counting may be caused due to the noise.

In the case of a light scattering method whereby particles are measured on the basis of scattered light, noise due to the light source and the light receiving element has a shape similar to that of a particle detection signal, and includes a wide range of frequency components. Accordingly, it is difficult to distinguish the noise by filtering, and false counting due to the noise may be caused.

An object of the present disclosure is to obtain a particle counter with which, by reducing false counting due to noise, particles can be accurately counted for each particle size.

A particle counter according to an aspect of the present disclosure includes a light source that emits light; a light superimposition unit configured to superimpose two lights in a space; an irradiation optical system configured to irradiate a fluid flowing in a flow passage with one light among a plurality of lights obtained by branching the light from the light source to form a detection area; a detection optical system configured to make a scattered light in a direction different from an optical axis of the irradiation optical system, among scattered lights from particles contained in the fluid in the detection area, enter the light superimposition unit; a reference optical system configured to make another one light among the plurality of lights enter the light superimposition unit as a reference light; a detector configured to receive an interference light by the scattered light and the reference light with a light receiving element, the interference light being obtained by the light superimposition unit, the detector being configured to generate a detection signal corresponding to the interference light; a filter configured to perform, with respect to the detection signal generated by the detector, a filtering process for passing a frequency component corresponding to an intensity change of the interference light; a determination unit configured to determine, from a peak level of the detection signal before filtering and a peak level of the detection signal after filtering, whether the detection signal is due to the particle, according to a predetermined calculation formula; and a counting unit configured to perform, if it is determined by the determination unit that the detection signal is due to the particle, particle counting based on the detection signal after filtering, and not to perform, if it is not determined by the determination unit that the detection signal is due to the particle, the particle counting based on the detection signal after filtering.

Furthermore, the predetermined calculation formula is $(Vp1-Vp2)/Vp1$ for determining an attenuation rate from the peak level $Vp1$ of the detection signal before filtering to the peak level $Vp2$ of the detection signal after filtering.

According to the above embodiment of the present disclosure, a particle counter is obtained with which, by reducing false counting due to noise, particles can be accurately counted for each particle size.

In the following, embodiments of the present disclosure will be described with reference to the drawings.

First Embodiment

FIG. 1 is a block diagram of a configuration of a particle counter according to a first embodiment of the present disclosure. The particle counter illustrated in FIG. 1 is provided with a light source 1, a flow cell 2, an optical system 3, a detector 4, a filter 5, a determination unit 6, and a counting unit 7.

The light source 1 is a light source that emits a predetermined wavelength of light (herein, laser light). In the present embodiment, the light source 1 emits a single-mode, highly coherent light. For example, as the light source 1, a laser light source having a wavelength of 532 nm and an output on the order of 500 mW is used.

The flow cell 2 forms a flow passage for a fluid containing particles to be counted. In the embodiment, the fluid containing particles to be counted is a liquid.

Figure 2:
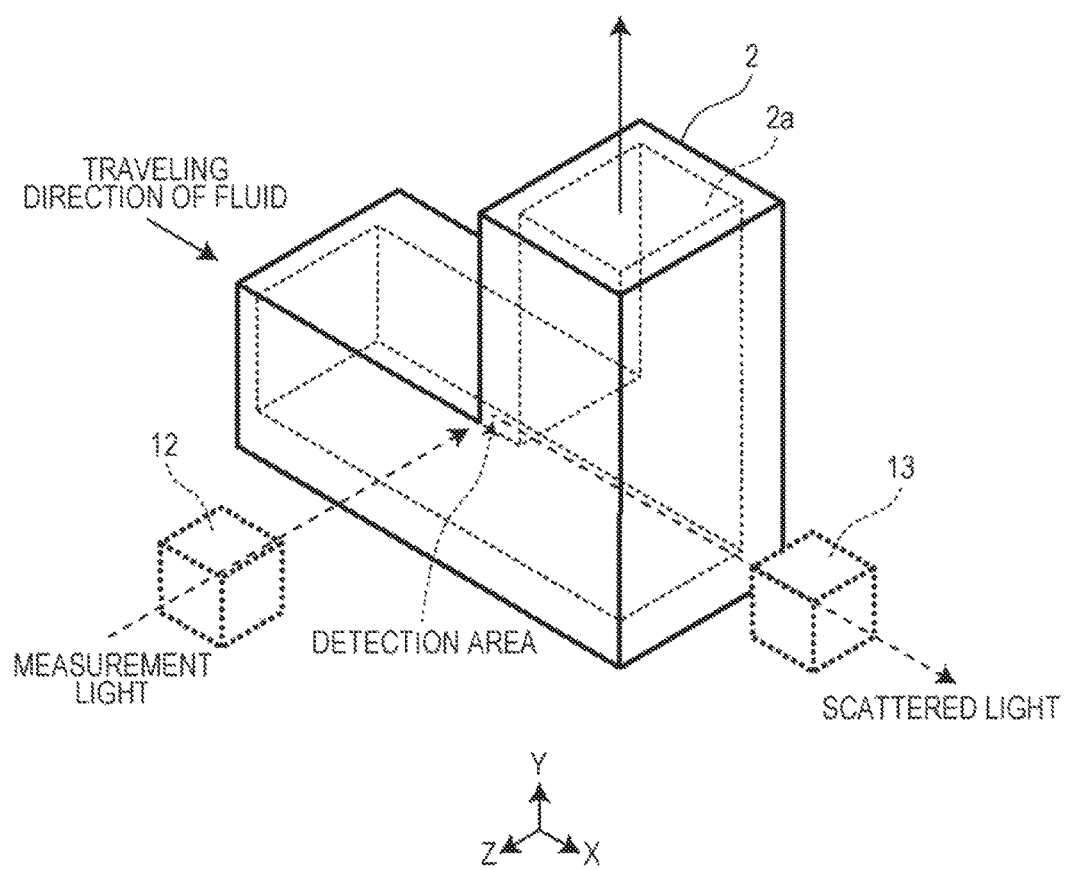
FIG. 2 is a perspective view of an example of a flow cell in FIG. 1.

FIG. 2 is a perspective view of an example of the flow cell 2 illustrated in FIG. 1. As illustrated in FIG. 2, the flow cell 2 is bent in an L shape. The flow cell 2 is a transparent tubular member that forms a bent flow passage $2a$. When the fluid containing particles to be counted is a chemical solution such as isopropyl alcohol, hydrofluoric acid solution, or acetone, the flow cell 2 made from sapphire is used, for example.

In the flow cell 2, the fluid flowing in the flow passage $2a$ is irradiated with one light among lights obtained by branching a light from the light source 1, to form a detection area.

The optical system 3 includes a beam splitter 11, an irradiation optical system 12, a detection optical system 13, an attenuator 14, a mirror 15, a beam expander 16, a beam splitter 17, and condensers $18a$ and $18b$.

The beam splitter 11 branches a light from the light source 1 into two lights. One of the lights branched by the beam splitter 11 (hereinafter, called measurement light) enters the irradiation optical system 12. The other light among the lights branched by the beam splitter 11 (hereinafter, called reference light) enters the attenuator 14. For example, the beam splitter 11 branches the light from the light source 1 at a predetermined unequal ratio (for example, 90:10). The intensity of the measurement light is greater than the intensity of the reference light.

The irradiation optical system 12 irradiates the fluid flowing in the flow passage $2a$ with the measurement light from a direction (in this example, the vertical direction, namely, a Z direction in FIG. 2) different from a traveling direction of the fluid in the flow passage $2a$ of the flow cell 2 (an X direction in FIG. 2). The irradiation optical system 12 uses a lens group as described in JP-A-2003-270120, for example, to shape the laser beam in such a manner as to enhance its energy density.

The detection optical system 13 makes the scattered light from the particles in the flow passage $2a$ by the foregoing irradiation with the measurement light enter a predetermined incident surface of the beam splitter 17. For example, the detection optical system 13 uses a condensing lens or an optical system including a pin hole for blocking background light and condensing lenses arranged on the front and rear stages of the pin hole.

In the embodiment, the measurement light enters the flow passage $2a$ from a direction different from the optical axis of the detection optical system 13. Accordingly, the detection optical system 13 makes the scattered light of side scattering enter the beam splitter 17.

Figure 3:
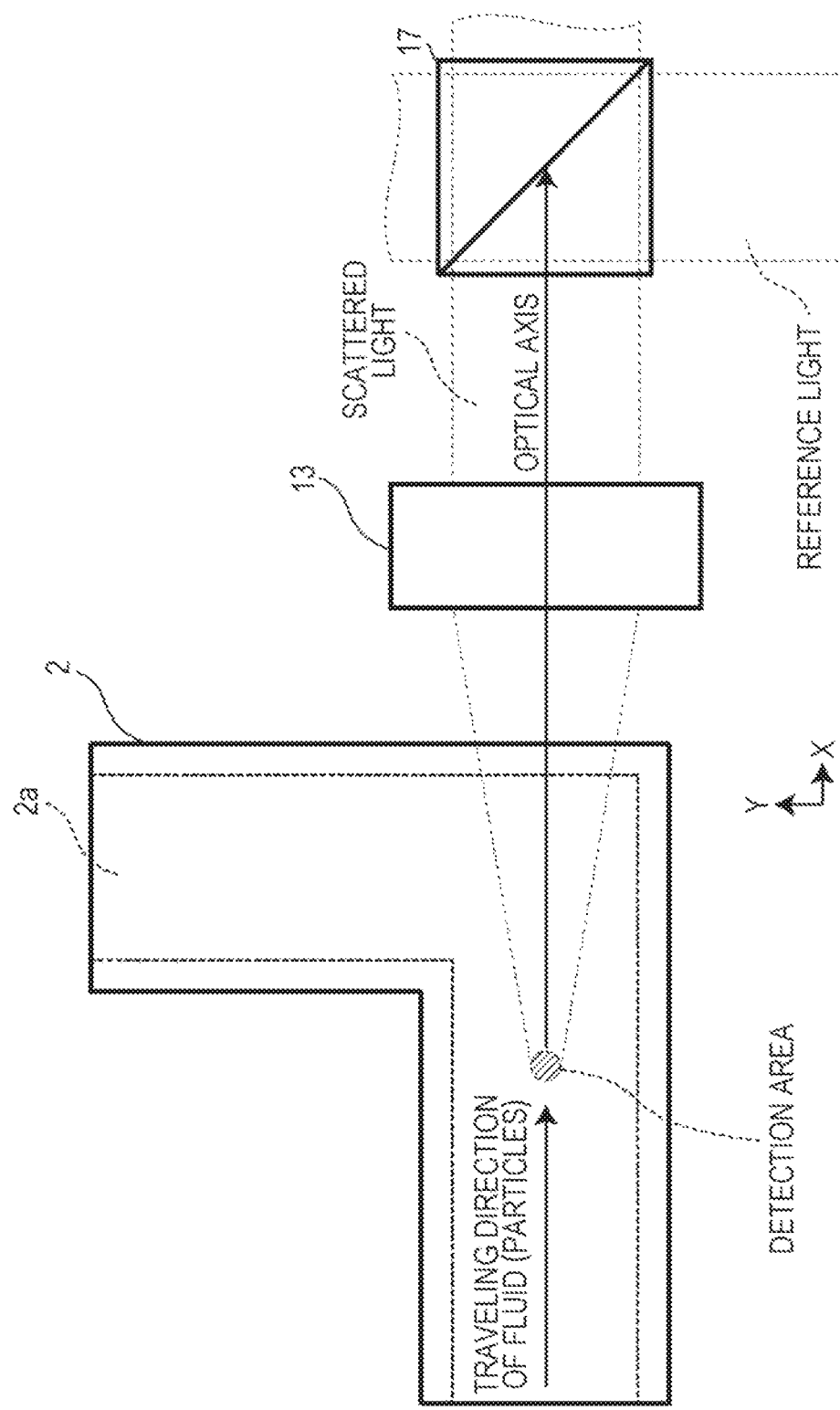
FIG. 3 is a diagram for describing an arrangement of the flow cell, a detection optical system, and a beam splitter in FIG. 1.

FIG. 3 is a drawing for describing the arrangement of the flow cell 2, the detection optical system 13, and the beam splitter 17 illustrated in FIG. 1. Specifically, as illustrated in FIG. 3, the detection optical system 13 makes a scattered light emitted along the traveling direction of the fluid (from the other perspective, the particles) in the detection area enter the beam splitter 17 among scattered lights emitted from the particles and the fluid in the flow passage $2a$.

In the embodiment, as illustrated in FIG. 3, the traveling direction (X direction) of the fluid (from the other perspective, the particles) is identical to the direction of the optical axis of the detection optical system 13. The scattered light within a predetermined solid angle from the center of the detection area enters the beam splitter 17.

Thus, among the scattered lights emitted from the particles in the flow passage $2a$, the side scattered light emitted along the traveling direction (X direction) of the fluid in the detection area is detected. Accordingly, a change in an optical path length, which is the distance between the particles and the beam splitter 17, in association with the movement of the particles in the detection area becomes greater than in the case of the detection of the scattered lights from the particles in another direction (a direction other than the X direction). This point will be described later.

Meanwhile, the reference light branched by the beam splitter 11 enters the attenuator 14.

The attenuator 14 attenuates the intensity of the light at a predetermined ratio. As the attenuator 14, a neutral density (ND) filter is used, for example. The mirror 15 reflects the reference light emitted from the attenuator 14 and makes the reference light enter the beam expander 16. For example, the beam splitter 11 and the attenuator 14 configure the intensity of the reference light to be approximately one ten thousandth of the intensity of the light emitted from the light source 1. The intensity of the reference light that enters the beam splitter 17 is set according to the particle size of the particles to be counted, the intensity of the scattered light, and the like. The attenuation rate of the attenuator 14 and the like are set to achieve the intensity of the reference light.

The beam expander 16 enlarges a beam diameter of the reference light to a predetermined diameter. The beam expander 16 employs the reference light with the enlarged beam diameter as an approximately parallel light and makes the approximately parallel light enter a predetermined incident surface (an incident surface different from the incident surface of the scattered light) of the beam splitter 17.

In the present embodiment, the detection optical system 13, the mirror 15, and the beam expander 16 are set such that, in the beam splitter 17, the wavefront shape of the scattered light of a particle and the wavefront shape of the reference light are substantially matched with each other. In the present embodiment, the detection optical system 13 and the beam expander 16 respectively emit the scattered light and the reference light as approximately parallel light. The wavefront shapes of the scattered light and the reference light may be curved.

In addition, the detection optical system 13, the mirror 15, and the beam expander 16 are configured such that their polarizing angles at the beam splitter 17 match with one another.

Thus, in the embodiment, to further enhance the degree of interference, the attenuator 14, the mirror 15, the beam expander 16, and others are set in the optical path of the reference light to control the intensity, a polarizing angle, and a wave front shape of the reference light.

The beam splitter 17 superimposes the incident scattered light and the incident reference light in a space so that they interfere with each other constructively or destructively. In the present embodiment, the beam splitter 17 is provided separately from the beam splitter 11. In the beam splitter 17, a phase difference between the scattered light and the reference light changes in accordance with a change in the optical path length as a result of the movement of a particle in the detection area. Further, the intensity of the interference light changes due to light that is transmitted through or reflected by the beam splitter 17 itself, as will be described later. As described above, the side scattered light emitted along the traveling direction of the fluid in the detection area is detected. In this way, compared with a case in which light emitted in other directions is detected, the optical path length of the scattered light due to the movement of the particle in the detection area changes more and faster. Accordingly, the rate of the intensity change of the interference light also increases. Thus, the intensity of the interference light changes in a period (i.e., frequency) corresponding to the velocity of the fluid (i.e., particle) in the traveling direction in the detection area. In a period in which the scattered light due to the particle is not entered, a transmitted component of the scattered light due to fluid and a reflected component of the reference light are emitted from the beam splitter 17 while interfering with each other, and a reflected component of the scattered light due to fluid and a transmitted component of the reference light are emitted therefrom while interfering with each other. In this case, the molecules of the fluid are extremely small and extremely large in number. Accordingly, the scattered light due to the molecules is random, and a change in the interference light due to the molecules is small compared with a change due to the particle.

The condenser 18a condenses light emitted from one emission surface of the beam splitter 17 and makes the light enter a light receiving element 21a. The condenser 18b condenses the light emitted from another emission surface of the beam splitter 17 and makes the light enter the light receiving element 21b. As the condensers 18a and 18b, condensing lenses are used, for example.

Figure 4:
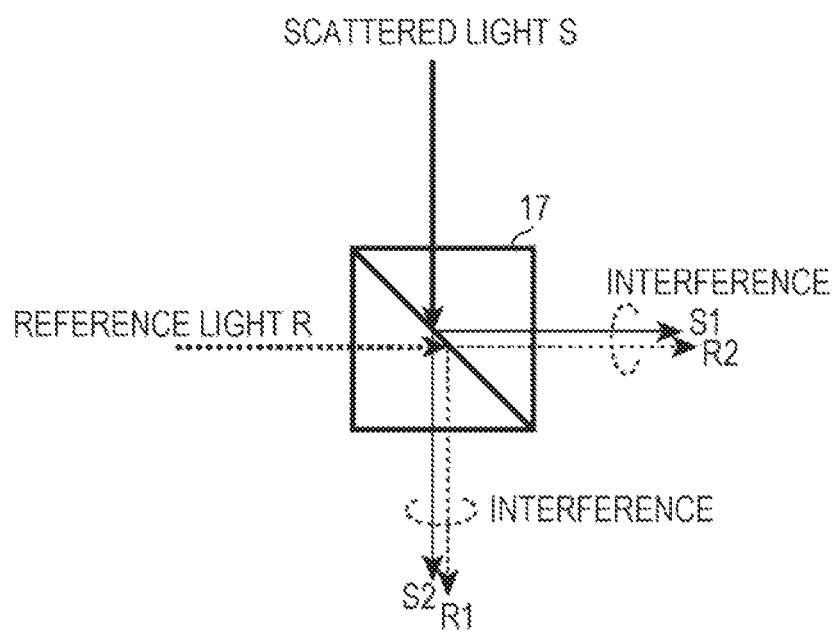
FIG. 4 is a diagram for describing the branching of light in the beam splitter of FIG. 1.

FIG. 4 is a diagram for describing the branching of light in the beam splitter 17 of FIG. 1. As illustrated in FIG. 4, scattered light S and reference light R enter the beam splitter 17 in such a way that the optical axis of a reflected component S1 of the scattered light S and the optical axis of a transmitted component R2 of the reference light R are aligned with each other, and such that the optical axis of a transmitted component S2 of the scattered light S and the optical axis of a reflected component R1 of the reference light R are aligned with each other. Accordingly, the beam splitter 17 emits first interference light due to the reflected component S1 of the scattered light S and the transmitted component R2 of the reference light R, and second interference light due to the transmitted component S2 of the scattered light S and the reflected component R1 of the reference light R. The first interference light and the second interference light respectively enter light receiving elements 21a and 21b of the detector 4 via condensers 18a and 18b.

The scattered light S and the reference light R respectively enter a light branching surface of the beam splitter 17 at approximately 45 degrees. The transmitted components S2 and R2 respectively have the same phases as those of the scattered light S and the reference light R. The phases of the reflected components S1 and R1 respectively lag by 90 degrees with respect to the scattered light S and reference light R. Accordingly, an intensity change of the first interference light and an intensity change of the second interference light are opposite in phase, as will be described later.

In addition, preferably, the ratio of the transmitted component to the reflected component in the beam splitter 17 is 50:50. However, the ratio may be unequal such as 60:40. When the ratio of the transmitted component to the reflected component in the beam splitter 17 is unequal, the gains of amplifiers 22a and 22b are set according to the ratio such that the transmitted component of the reference light in an electrical signal V1 and the reflected component of the reference light in an electrical signal V2 become equal.

A beam damper 19 absorbs the light having passed through the flow cell 2. This ensures restraining the influence on the optical system 3 caused by irregular light reflection, leakage, and others of the light having passed through the flow cell 2.

The detector 4 receives the interference lights from the beam splitter 17 with the light receiving elements 21a and 21b. The detector 4 generates a detection signal Vo corresponding to a difference between the interference lights. In the present embodiment, as illustrated in FIG. 1, the detector 4 is provided with the light receiving elements 21a and 21b, the amplifiers 22a and 22b, and a difference calculator 23.

The light receiving elements 21a and 21b are photodetectors such as a photodiode and a phototransistor and each outputs the electrical signals corresponding to the incident lights. The amplifiers 22a and 22b amplify the electrical signals output from the light receiving elements 21a and 21b by predetermined gains. The difference calculator 23 calculates the difference between the electrical signal V1, which is obtained by the light receiving element 21a and corresponds to the first interference light, and the electrical signal V2, which is obtained by the light receiving element 21b and corresponds to the second interference light, and outputs this difference as the detection signal Vo.

In a state where a scattered light component due to the particles is not contained (the scattered light component due to the fluid and a reference light component), the gains of the amplifiers 22a and 22b are adjusted such that a voltage of the electrical signal V1 becomes identical to a voltage of the electrical signal V2. Instead, one of the amplifiers 22a and 22b may be disposed and the gain of the amplifier may be adjusted so as to match both of the foregoing voltages. In the case where the voltage of the electrical signal of the light receiving element 21a is identical to the voltage of the electrical signal of the light receiving element 21b, the amplifiers 22a and 22b may be omitted.

Figure 5:
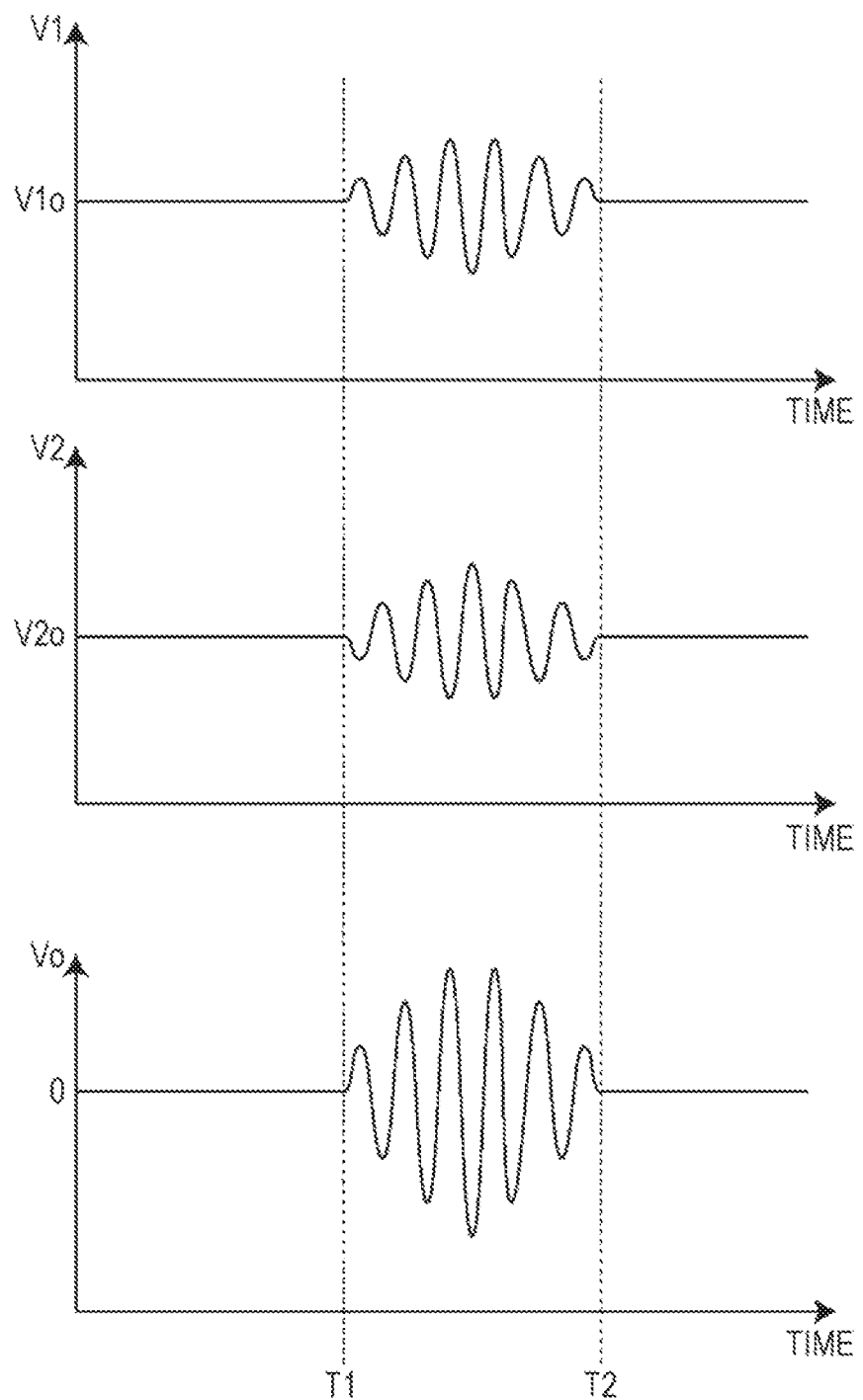
FIG. 5 shows timing charts for describing a detection signal obtained by a detector in FIG. 1.

FIG. 5 is a timing chart describing the detection signal obtained by the detector 4 illustrated FIG. 1.

When a certain particle passes through the detection area during a period of time T1 to time T2, a scattered light is generated due to the particles in that period. Then, as the particle moves in the traveling direction (X direction) in the detection area, the optical path length from the particle to the light branch surface of the beam splitter 17 changes. Accordingly, the phase difference between the scattered light due to the particles and the reference light changes. The intensity of the interference light (amplitude) changes to strengthen or weaken mutually.

Accordingly, as illustrated in FIG. 5, the electrical signal V1 varies, in a period in which the particle passes through the detection area, positively or negatively with reference to a voltage V1o in a particle-absent state, depending on the degree of interference. Similarly, the electrical signal V2 varies, in a period in which the particle passes through the detection area, positively or negatively with reference to a voltage V2o in the particle-absent state, depending on the degree of interference. The alternating-current components of the electrical signals V1 and V2 in that period are opposite in phase to each other.

The reference voltages V1o and V2o of the electrical signals V1 and V2 output from the amplifiers 22a and 22b are equal to one another. Accordingly, as illustrated in FIG. 5, the detection signal Vo obtained by the difference calculator 23 has an AC component with an amplitude greater (about double) than that of the AC component resulting from the interferences of the respective electrical signals V1 and V2 in the period during which the particles pass through the detection area. The detection signal Vo has a voltage of almost zero except for the period.

In the present embodiment, the scattered light emitted along the traveling direction (X-direction) of the fluid in the detection area is detected. In this way, the change in the optical path length when the particle passes through the detection area becomes greater. When the particle passes through in the period from time T1 to time T2, the distance of movement of the particle corresponds to the change in the optical path length between the particle and the light branching surface of the beam splitter 17. Accordingly, compared to when the scattered light of the particle is detected in other directions (other than the X-direction), the number of times of change in interference increases (that is, the rate of the intensity change of the interference light becomes greater, and phase rotation of the interference light increases). This means that in the period from time T1 to time T2, the number of waves of the electrical signals output from the light receiving elements 21a and 21b is increased. Consequently, signal detection becomes more likely, and the S/N ratio improves. However, as long as the scattered light can be detected, the direction of detection of the scattered light is not limited.

The scattered light (background light) from the liquid as a fluid medium is generated in the entire detection area. Further, background lights from different positions are also present. However, the background lights are canceled out by the difference calculation. Accordingly, the AC component of the detection signal Vo resulting from the interference of the background light is smaller than the AC component resulting from the interference of the scattered light due to the particles.

In the present embodiment, the particle size of the particles to be counted is smaller than the wavelength of the light emitted from the light source 1. Accordingly, the intensity of the scattered light due to Rayleigh scattering is proportional to the sixth power of the particle size. Meanwhile, the intensity of the interference light by the scattered light and the reference light is proportional to the third power of the particle size according to the relational expression ($I \propto Er \cdot ED1 \, (D1/D0)^3$) of particle size and intensity I of the interference light. Accordingly, the decrease in optical intensity when the particle size is reduced is smaller when the interference light is detected than when the scattered light is directly detected. In the relational expression, D0 and D1 are particle sizes, Er is the electric field intensity of the reference light, and ED1 is the electric field intensity of the scattered light from particle D1.

The difference between the maximum value and the minimum value of the intensity of the interference light by the scattered light and the reference light (the interference light intensity difference between when the phase difference between the scattered light and the reference light is zero and when the phase difference is 180 degrees) is proportional to the product of the electric field intensity Er of the reference light and an electric field intensity Es of the scattered light. Accordingly, by increasing the intensities of the scattered light and the reference light, sufficiently strong interference light can be obtained. As a result, a detection signal with a sufficiently large amplitude can be obtained. The intensity of the reference light is set, in accordance with the dynamic ranges of the detector 4, the filter 5, and the counting unit 7, to a value such that the detection signal can be processed in a preferable manner.

For example, when a scattered light intensity Is of a particle with a particle size of 20 nm is $7.0 \times 10^{-6}$ μW, the scattered light intensity Is is converted into a scattered light intensity I per unit area, wherein the electric field intensity Es of the scattered light is determined to be approximately $5.8 \times 10^{-3}$ V/m, according to the relational expression ($I = 0.5 \cdot c \cdot \varepsilon \cdot Es^2$) of optical intensity and electric field intensity. Meanwhile, when a reference light intensity Ir is 1.2 μW, the electric field intensity Er of the reference light is approximately 2.4 V/m. If the scattered light and the reference light interfere with each other in the entire wavefront area, the interference light intensity difference ($2 \cdot c \cdot \varepsilon \cdot Es \cdot Er \cdot$ unit area) is approximately $1.2 \times 10^{-2}$ μW, which is approximately 1600 times the scattered light intensity, indicating the same level of amplification as for the scattered light intensity of a particle with a particle size of 70 nm. Herein, c is the speed of light (m/s), and c is the dielectric constant (F/m) of air.

The filter 5 performs, with respect to the detection signal Vo generated by the detector 4, a filtering process for passing the frequency component corresponding to the intensity change of the interference light. In the present embodiment, the filter 5 is a band-pass filter which attenuates frequency components other than a substantially single frequency component corresponding to the intensity change of interference light. The band-pass filter has a pass-band set such that the frequency component corresponding to the fluid velocity (i.e., moving velocity of particle) in the flow passage 2a (namely, a frequency component corresponding to the intensity change of the interference light) is passed, and such that frequency components other than the frequency component corresponding to the traveling rate of fluid are attenuated. In this way, the noise component of the detection signal Vo is attenuated, and the S/N ratio of the detection signal Vo becomes higher. The pass-band frequency is specified in advance based on the moving velocity of particle, the wavelength of the measurement light (i.e., the wavelength of the light source 1), and the like. If the noise frequency is higher than the frequency corresponding to the intensity change of the interference light, a low-pass filter may be used. If the noise frequency is lower than the frequency corresponding to the intensity change of the interference light, a high-pass filter may be used.

The determination unit 6 determines, from a peak level Vp1 of the detection signal Vo before filtering and a peak level Vp2 of the detection signal Vo1 after filtering and according to a predetermined calculation formula, whether the detection signal Vo is due to a particle. For example, the predetermined calculation formula is (Vp1−Vp2)/Vp1 for determining an attenuation rate.

Figure 6:
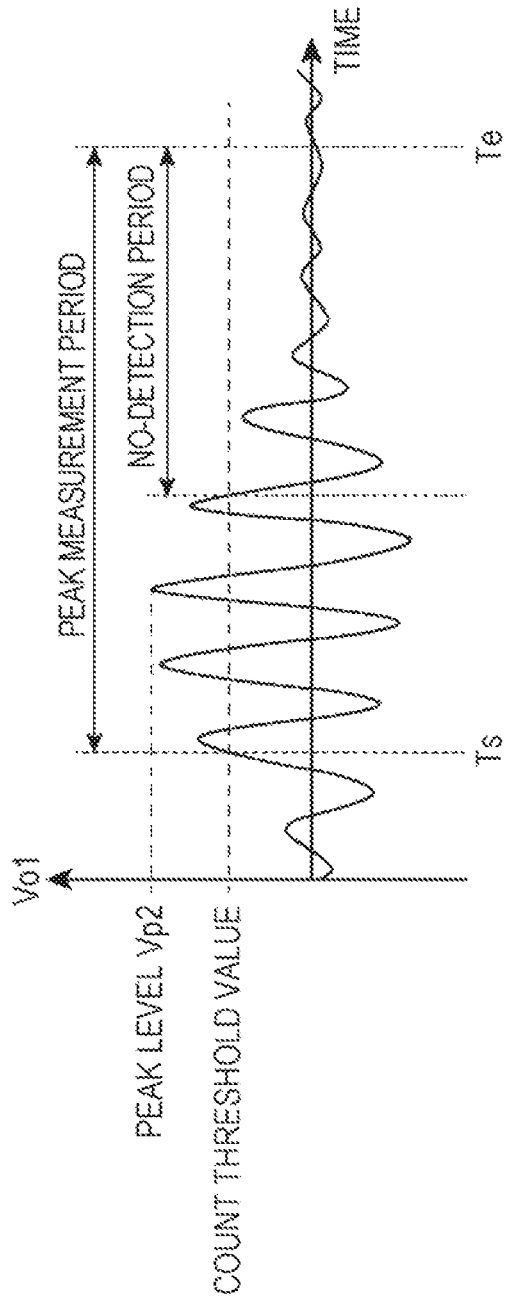
FIG. 6 is a diagram for describing peak level detection by a determination unit of FIG. 1.

FIG. 6 is a diagram for describing peak level detection by the determination unit 6 of FIG. 1. As illustrated in FIG. 6, the determination unit 6 starts a peak measurement period from a point in time Ts at which the detection signal exceeded a predetermined threshold value (count threshold value). The determination unit 6 ends the peak measurement period at a point in time Te at which a detection signal exceeding the count threshold value has not been detected in a predetermined length of no-detection period. The determination unit 6 detects a maximum value of the detection signal in the peak measurement period as a peak level for the peak measurement period. FIG. 6 illustrates the detection of a peak level Vp2 of the detection signal Vo1 after filtering. A peak level Vp1 of the detection signal Vo before filtering is similarly detected. The threshold value before filtering may be different from the count threshold value after filtering.

The counting unit 7, if it is determined by the determination unit 6 that the detection signal Vo is due to a particle, performs particle counting based on the detection signal Vo1 after filtering. On the other hand, if it is not determined by the determination unit 6 that the detection signal is due to a particle, the counting unit 7 does not perform the particle counting based on the detection signal Vo1 after filtering. For example, when the attenuation rate is calculated as (Vp1−Vp2)/Vp1, the determination unit 6, if the attenuation rate is not more than an attenuation rate threshold value (such as 50%), determines that the detection signal Vo is due to a particle. On the other hand, if the attenuation rate is greater than the attenuation rate threshold value, the determination unit 6 determines that the detection signal Vo is due to noise and the like, and does not determine that the detection signal Vo is due to a particle.

In the present embodiment, the determination unit 6, with respect to the detection signal Vo1 after filtering that exceeds the count threshold value, compares the attenuation rate threshold value with the attenuation rate. The determination unit 6, on the basis of the result of comparison, determines whether the detection signal Vo is due to a particle. Further, the counting unit 7 performs particle counting based on the detection signal Vo1 after filtering, as will be described later. One of the attenuation rate threshold value and the count threshold value is set depending on the other of the attenuation rate threshold value and the count threshold value. For example, when the attenuation rate is calculated as (Vp1−Vp2)/Vp1, the count threshold value may be set lower as the attenuation rate threshold value becomes lower.

When the particle counting is performed, the counting unit 7, for example, upon detection of an alternating-current component (i.e., the frequency component corresponding to the intensity change of the interference light) that continues in the above-described period of the detection signal Vo1, compares the amplitude of the alternating-current component with a predetermined threshold value that is determined for each particle size. The counting unit 7 counts individual particles separately for each particle size.

Figure 7:
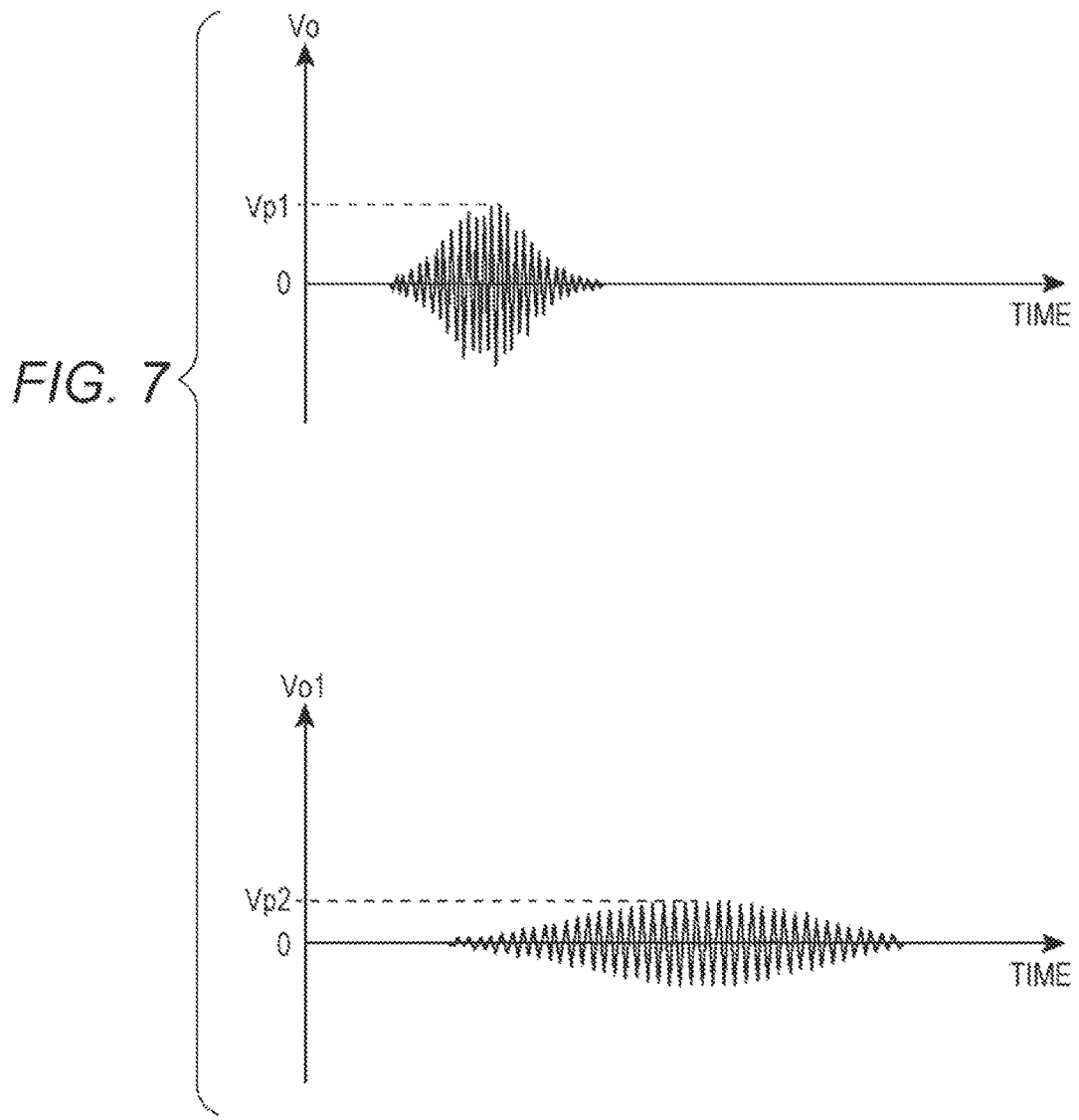
FIG. 7 illustrates examples of a waveform before filtering and a waveform after filtering of a detection signal due to a particle.
Figure 8:
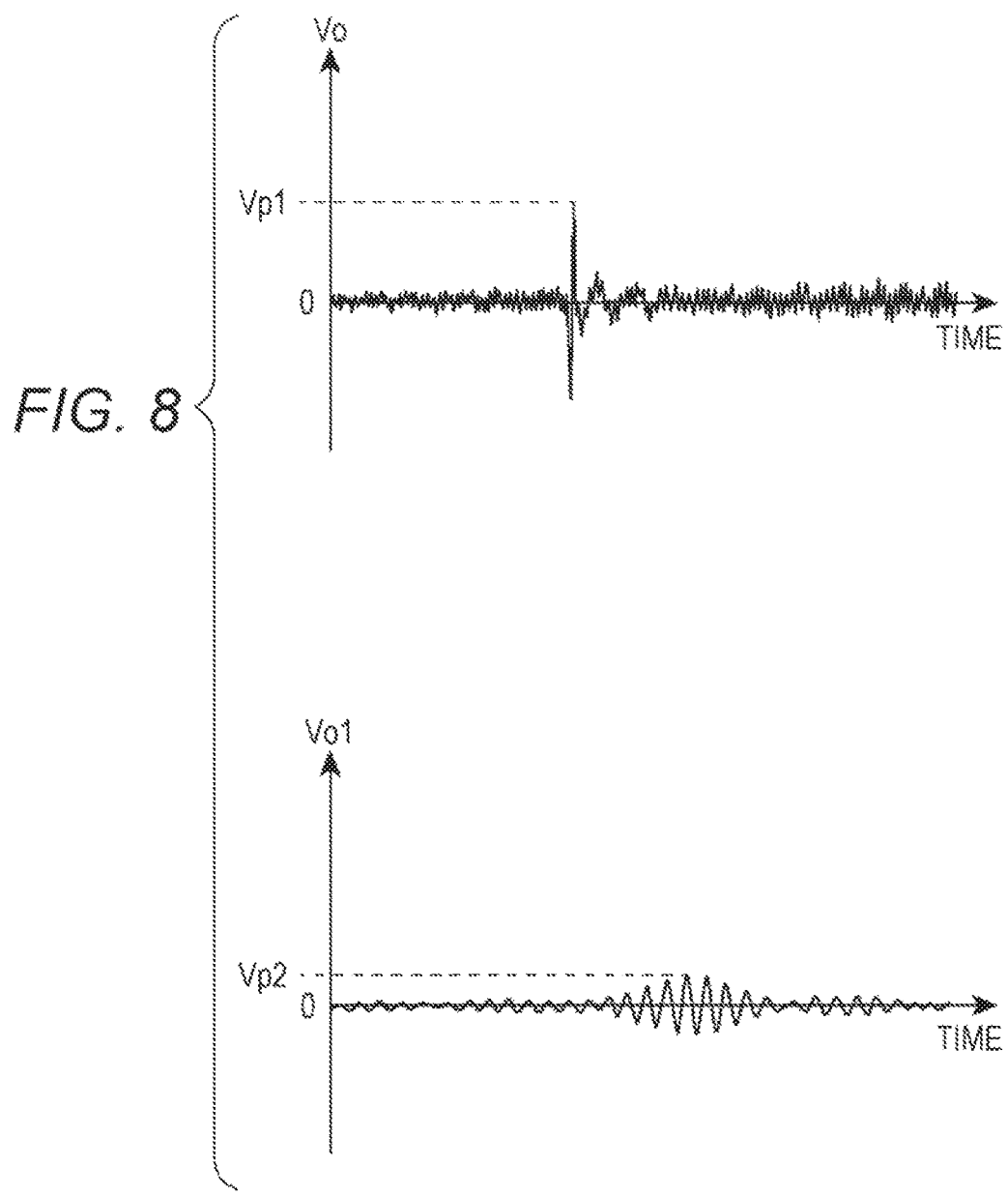
FIG. 8 illustrates examples of a waveform before filtering and a waveform after filtering of a detection signal due to spike noise.

FIG. 7 illustrates examples of the waveform before filtering and the waveform after filtering of a detection signal due to a particle. FIG. 8 illustrates examples of the waveform before filtering and the waveform after filtering of a detection signal due to spike noise.

For example, as illustrated in FIG. 7, when the detection signal is due to a particle, the detection signal Vo before filtering exhibits a waveform as if a substantially single frequency were amplitude-modulated with a low frequency. When the detection signal is due to a particle, the components of the detection signal Vo that pass through the filter 5 are increased. As a result, the attenuation rate of the detection signal Vo1 after filtering becomes lower (that is, the peak level of the detection signal Vo1 after filtering becomes comparatively higher).

On the other hand, when the detection signal is due to spike noise, as illustrated in FIG. 8, for example, the detection signal Vo before filtering has a wide range of frequency components. Accordingly, the components of the detection signal Vo that pass through the filter 5 are decreased, and the attenuation rate of the detection signal Vo1 after filtering becomes higher (that is, the peak level of the detection signal Vo1 after filtering becomes comparatively lower).

Thus, using the attenuation rate, it is possible to distinguish a detection signal due to a particle from a detection signal due to noise.

Next, operations of the particle counter according to the first embodiment will be explained.

The light source 1 emits the laser light. The beam splitter 11 branches the laser light into the measurement light and the reference light. After being attenuated by the attenuator 14, the reference light goes through the mirror 15 and the beam expander 16 and then is made to enter the beam splitter 17 as the approximately parallel light.

Meanwhile, the irradiation optical system 12 makes the measurement light enter the detection area in the flow cell 2. When a particle passes through the detection area, a scattered light is generated due to the particle during the period of the particle passing through the detection area. The detection optical system 13 makes scattered light emitted along the traveling direction (X direction) of the fluid in the flow passage 2a of the flow cell 2 enter the beam splitter 17 as approximately parallel light.

Thus, in the period during which the particles pass through the detection area, the reference light and the scattered light from the particles are made to enter the beam splitter 17. The beam splitter 17 emits the interference lights resulting from the interference between the scattered light and the reference light.

In the period during which the particles pass through the detection area, the beam splitter 17 emits the interference lights, and the interference lights are received by the respective light receiving elements 21a and 21b. The detector 4 outputs the electrical signal corresponding to the intensities of the interference lights as the detection signal Vo. Particularly, in the first embodiment, the detection signal Vo is generated based on the difference between the foregoing first interference light and the foregoing second interference light being opposite in phases to each other. Accordingly, the detection signal Vo of the AC components having an amplitude about two times of the electrical signals V1 and V2 is obtained.

The filter 5 performs a filtering process, with respect to the detection signal, to pass the frequency component corresponding to the intensity change of the interference light.

The determination unit 6, on the basis of the attenuation rate from the peak level Vp1 of the detection signal Vo before filtering to the peak level Vp2 of the detection signal Vo1 after filtering, determines whether the detection signal is due to a particle. If it is determined by the determination unit 6 that the detection signal is due to a particle, the counting unit 7 performs particle counting based on the detection signal Vo1 after filtering. On the other hand, if it is not determined by the determination unit 6 that the detection signal Vo is due to a particle, the counting unit 7 does not perform the particle counting based on the detection signal Vo1 after filtering.

As described above, in the particle counter according to the embodiment, the irradiation optical system 12 forms a detection area by irradiating, from a direction different from the direction of fluid flow, the fluid in the flow passage 2a with one of a plurality of lights obtained by branching the light from the light source 1. The detection optical system 13 makes scattered light which, from among scattered light from a particle contained in the fluid in the detection area, is in a direction different from the optical axis of the irradiation optical system 12 enter the beam splitter 17. Meanwhile, the beam expander 16 makes another light from among the plurality of lights enter the beam splitter 17 as the reference light. The detector 4 receives, with the light receiving elements, the interference light by the scattered light and the reference light obtained by means of the beam splitter 17, and generates a detection signal corresponding to the interference light. The filter 5 performs a filtering process, with respect to the detection signal generated by the detector 4, for passing the frequency component corresponding to an intensity change of the interference light. The determination unit 6, from the peak level of the detection signal before filtering and the peak level of the detection signal after filtering, determines whether the detection signal is due to a particle, according to a predetermined calculation formula. The counting unit 7, if it is determined by the determination unit 6 that the detection signal is due to a particle, performs particle counting based on the detection signal after filtering. On the other hand, the counting unit 7, if it is not determined by the determination unit 6 that the detection signal is due to a particle, does not perform the particle counting based on the detection signal after filtering.

In the particle counter according to the embodiment, the determination unit 6 distinguishes between the detection signal due to a particle and the detection signal due to noise. Accordingly, the particle counter, by reducing false counting due to noise, is capable of accurately counting particles for each particle size.

Second Embodiment

In the first embodiment, the first interference light and the second interference light are received as interference lights by the scattered light from the particles and the reference light. The difference between the electrical signals V1 and V2 of both is used as the detection signal Vo. In the second embodiment, instead of this, the electrical signal from either the first interference light or the second interference light is used as the detection signal Vo. In this case, the detection signal Vo also contains an AC component resulting from the interference light by the scattered light from the particles and the reference light. Accordingly, the particles can be counted in the same manner. In this case, one light receiving element may be provided.

Other components of a particle counter according to the second embodiment are the same as those of the first embodiment, and descriptions thereof will be omitted.

Those skilled in the art will readily appreciate that various modifications and changes may be made to the foregoing embodiments without departing from the spirit and scope of the subject matter of the present disclosure, and without diminishing the intended advantages. It is therefore intended that such modifications and changes be included in the appended claims.

For example, the foregoing first and second embodiments include the beam expander 16 at the optical path for the reference light. Instead or additionally, a beam expander may be disposed at a preceding stage of the beam splitter 11. In the first and second embodiments, the one mirror 15 is used as illustrated in FIG. 1. Instead, three mirrors may be used to adjust three-dimensionally the direction of the optical path. In addition, in the first and second embodiments, the scattered light from the particles and the reference light are superimposed by the use of the beam splitter 17. Instead, a polarization prism may be used.

In the first and the second embodiments, the light source 1 is a light source that emits highly coherent laser light in single mode. Instead, a light source that emits laser light having relatively low coherency in multimode may be used. However, it is preferable to use a light source with an energy distribution such that an interference between the scattered light from a particle and the reference light occurs at any position in the detection area. The light source 1 is not limited to a light source that emits laser light, and may be configured to emit light other than laser light, such as LED light. The light source 1 only needs to be configured to emit light such that the optical path length difference between the reference light side and the particle scattered light side is not greater than the coherent length of the light emitted from the light source 1.

In the first and the second embodiments, the filter 5 and the counting unit 7 may be analog circuits or digital circuits. When the filter 5 and the counting unit 7 are digital circuits, an analog-digital conversion is performed with respect to the detection signal Vo in a stage prior to the filter 5.

In the first and second embodiments, as illustrated in FIG. 1, a so-called Mach-Zehnder interference optical system in which the branching of light and the superimposition of light are performed by the different beam splitters 11 and 17 is employed. Instead, a Michelson or any other types of interference optical system may be used.

In addition, the particle counters according to the first and second embodiments are liquid-borne particle counters. The particle counters according to the first and second embodiments may be applied to airborne particle counters.

The embodiments of the present disclosure may be applied to a particle counter.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A particle counter comprising:
a light source that emits light;
a light superimposition unit configured to superimpose two lights in a space;
an irradiation optical system configured to irradiate a fluid flowing in a flow passage with one light among a plurality of lights obtained by branching the light from the light source to form a detection area;
a detection optical system configured to make a scattered light in a direction different from an optical axis of the irradiation optical system, among scattered lights from particles contained in the fluid in the detection area, enter the light superimposition unit;
a reference optical system configured to make another one light among the plurality of lights enter the light superimposition unit as a reference light;
a detector configured to receive an interference light by the scattered light and the reference light with a light receiving element, the interference light being obtained by the light superimposition unit, the detector being configured to generate a detection signal corresponding to the interference light;
a filter configured to perform, with respect to the detection signal generated by the detector, a filtering process for passing a frequency component corresponding to an intensity change of the interference light;
a determination unit configured to determine, from a peak level of the detection signal before filtering and a peak level of the detection signal after filtering, whether the detection signal is due to the particle, according to a predetermined calculation formula; and
a counting unit configured to perform, if it is determined by the determination unit that the detection signal is due to the particle, particle counting based on the detection signal after filtering, and not to perform, if it is not determined by the determination unit that the detection signal is due to the particle, the particle counting based on the detection signal after filtering, wherein:
the predetermined calculation formula is $(Vp1-Vp2)/Vp1=$ an attenuation rate, where $Vp1$ represents the peak level of the detection signal before filtering and $Vp2$ represents the peak level of the detection signal after filtering, and
the determination unit determines, based on the result of comparison of an attenuation rate threshold value and the attenuation rate, whether the detection signal is due to the particle.

2. The particle counter according to claim 1, wherein:
the counting unit performs the particle counting, based on the result of comparison of a count threshold value and the detection signal after filtering; and
one of the attenuation rate threshold value and the count threshold value is set depending on the other of the attenuation rate threshold value and the count threshold value.

3. The particle counter according to claim 1, wherein the filter is a band-pass filter which attenuates frequency components other than the frequency component corresponding to the intensity change of the interference light.

4. The particle counter according to claim 2, wherein the filter is a band-pass filter which attenuates frequency components other than the frequency component corresponding to the intensity change of the interference light.

* * * * *